United States Patent
Ginggen et al.

(10) Patent No.: US 7,983,760 B2
(45) Date of Patent: Jul. 19, 2011

(54) CONTROL UNIT HAVING A DEPLOYABLE ANTENNA

(75) Inventors: Alec Ginggen, Neuchatel (CH); Thierry Pipoz, LeLocle (CH)

(73) Assignee: Codman & Shurtleff, Inc., Raynham, MA (US)

( * ) Notice: Subject to any disclaimer, the term of this patent is extended or adjusted under 35 U.S.C. 154(b) by 839 days.

(21) Appl. No.: 11/070,998

(22) Filed: Mar. 3, 2005

(65) Prior Publication Data

US 2006/0200209 A1    Sep. 7, 2006

(51) Int. Cl.
*A61N 1/08* (2006.01)
(52) U.S. Cl. ......................................................... 607/60
(58) Field of Classification Search .............. 607/59–61, 607/30–33
See application file for complete search history.

(56) References Cited

U.S. PATENT DOCUMENTS

| | | | |
|---|---|---|---|
| 4,441,498 A | 4/1984 | Nordling | |
| 6,115,634 A | 9/2000 | Donders | |
| 6,275,737 B1 * | 8/2001 | Mann | 607/61 |
| 2003/0055478 A1 | 3/2003 | Lyster | |
| 2004/0106967 A1 * | 6/2004 | Von Arx et al. | 607/60 |
| 2005/0075698 A1 * | 4/2005 | Phillips et al. | 607/61 |

* cited by examiner

*Primary Examiner* — Eric D. Bertram

(57) ABSTRACT

A control unit for an implantable medical device includes a housing and electronics within the housing. The electronics control an RF emission from the control unit. An antenna is pivotably connected to the housing. The antenna is movable between a stowed position where RF emission from the antenna is prevented and a deployed position where RF emission from the antenna is permitted. To use the external control unit to effect communication between an external control unit and an implanted medical device, the user places the external control unit within electronic communication range of the implanted medical device. The control unit antenna is moved from the stowed position to a deployed position where RF emission from the antenna is permitted. RF waves are emitted from the antenna to establish communication between the external control unit and the implanted medical device.

10 Claims, 2 Drawing Sheets

FIG. 2
FIG. 2A
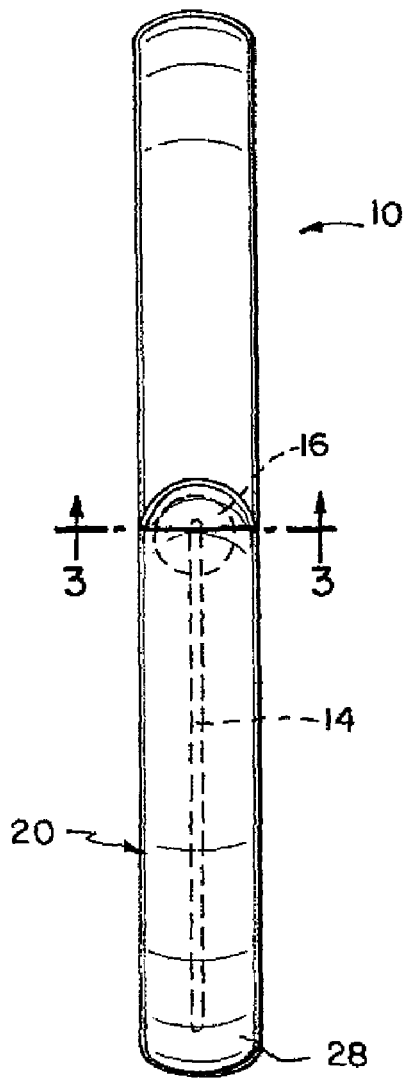
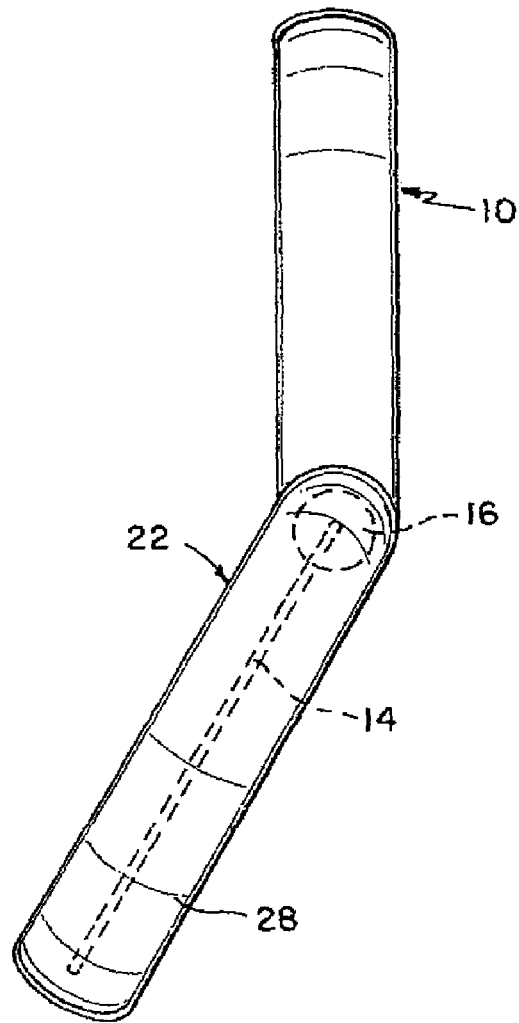
FIG. 3
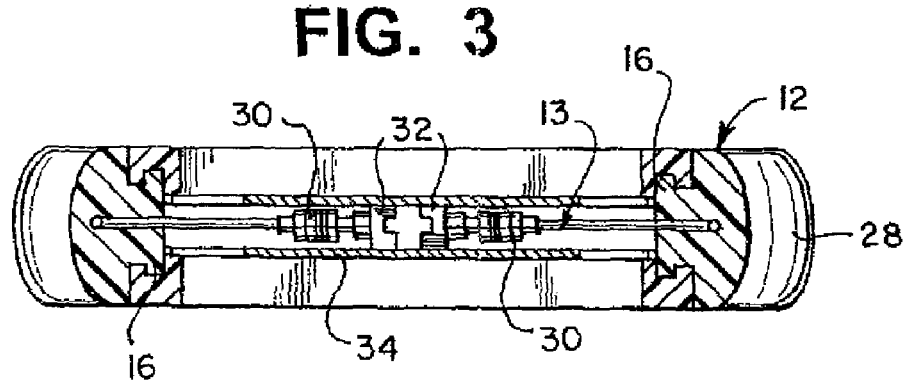

CONTROL UNIT HAVING A DEPLOYABLE ANTENNA

FIELD OF THE INVENTION

The present invention relates generally to a control unit having a deployable antenna. More specifically, the present invention relates to an external control unit for communicating with an implantable medical device, which control unit has an antenna that pivots between a stowed position and a deployed position.

BACKGROUND OF THE INVENTION

Inductive coupling has become the method of choice for energy and data transmission between an external control unit and an implanted medical device, such as, for example, an infusion pump, a pacemaker or a defibrillator. To effect this communication, both the external control unit and the implantable medical devices must have an antenna so that they can communicate, usually by radio-frequency ("RF") telemetry. The antennas are typically made of coils of one or more turns. Optimal energy and data transmission is achieved with a control unit antenna made of a coaxial cable, which shield is broken at one point to allow for RF wave radiation. However, the position of the antenna is usually fixed with respect to the control unit housing. To communicate with an implanted medical device, RF waves are emitted from the antenna. However, these RF waves can interfere with the electronics inside the control unit housing and can affect the control unit functionality.

Others have attempted to overcome these problems by using a control unit that has an antenna connected to the control unit by a cable. These control units are usually the size of a laptop computer, which is too big to be carried by the user on a daily basis. Even if the control unit were of a hand held size, the user is still required to manage two pieces simultaneously: the control unit displaying the information to manage the communication, and the antenna to be positioned on top of the implant during the interrogation.

There are control units that are of a hand held size, except the antenna in these control units is integrated in the control unit housing. The antenna is mounted about the electronics within the control unit. Thus, the RF energy emitted by the antenna is limited to minimize the interference with the electronics within the control unit. But limiting the RF energy also limits the interrogation distance and the amount of energy that can be transmitted during an energy and data transmission.

Accordingly, there is a need for a control unit for an implantable medical device that has an antenna that can communicate with the implantable medical device without interfering, or at least substantially minimizing the interference, with the electronics inside the control unit housing.

SUMMARY OF THE INVENTION

The present invention provides a control unit that achieves these and other needs by providing a housing and electronics within the housing. The electronics control, inter alia, an RF emission from the control unit. An antenna is pivotably connected to the housing. The antenna is movable between a stowed position where RF emission from the antenna is prevented and a deployed position where RF emission from the antenna is permitted. To use the external control unit to effect communication between an external control unit and an implanted medical device, the user places the external control unit within electronic communication range of the implanted medical device. The control unit antenna is moved from the stowed position to a deployed position where RF emission from the antenna is permitted. RF waves are emitted from the antenna to establish communication between the external control unit and the implanted medical device.

BRIEF DESCRIPTION OF THE DRAWINGS

The invention will be more fully understood from the following detailed description taken in conjunction with the accompanying drawings, in which:

FIG. 2 is a side view of the control unit with the antenna in a deployed position;

FIG. 2A is a side view of the control unit with the antenna in a second deployed position;

FIG. 3 is a cross-sectional view taken along line 3-3 of FIG. 2 and looking in the direction of the arrows.

DETAILED DESCRIPTION OF THE INVENTION

Figure 1:
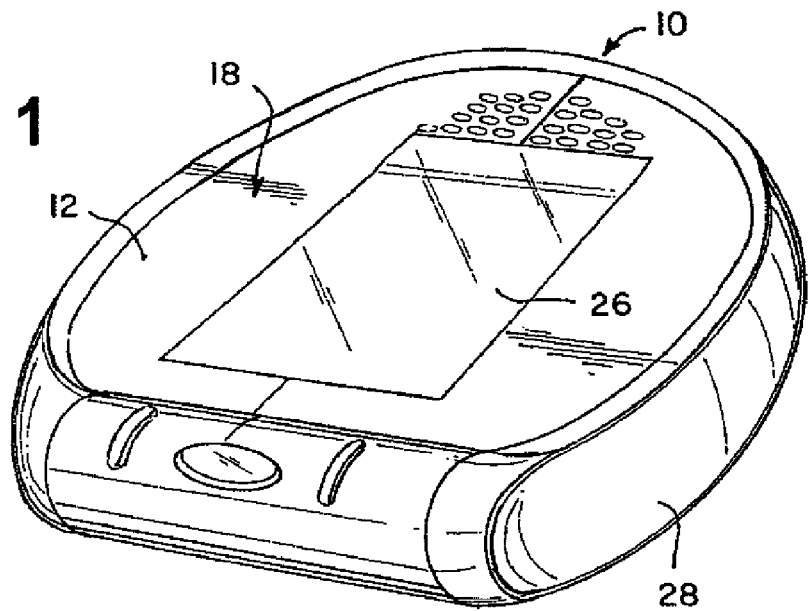
FIG. 1 is a perspective view of a control unit in accordance with the present invention with an antenna in a stowed position.
Figure 1A:
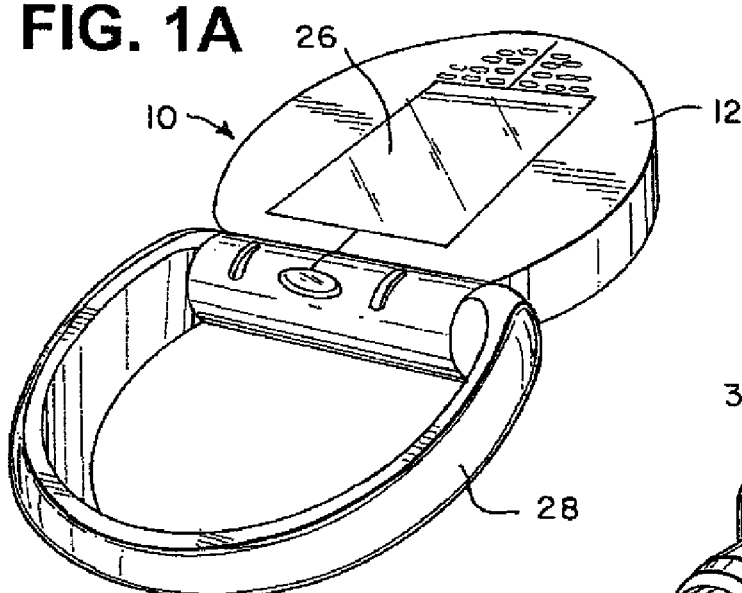
FIG. 1A a perspective view of a control unit in accordance with the present invention with an antenna in a deployed position.
Figure 4:
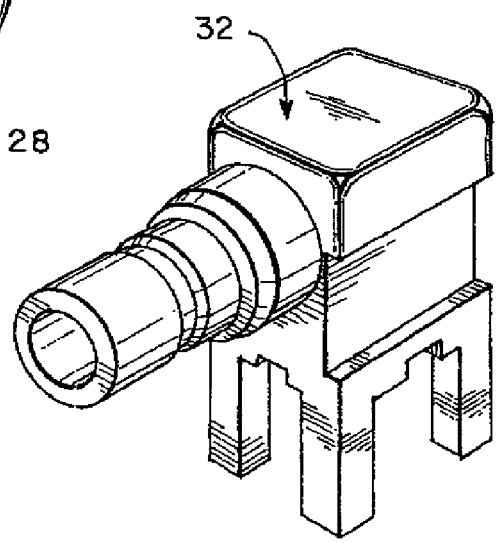
FIG. 4 is a perspective view of a right angle connector.

Referring now to FIGS. 1-4, a control unit 10 for an implantable medical device is illustrated. Control unit includes a housing 12. Electronics 13, for controlling an RF emission from the control unit, are disposed within housing 12. An antenna 14 is pivotably connected to housing 12 at connection 16. Antenna 14 is movable between a stowed position 18, as illustrated in FIG. 1, and two deployed positions 20, 22, as illustrated in FIGS. 2 and 3. The pivotable connection 16 between the antenna and the housing includes a switch electrically connected to the electronics to detect the position of the antenna. The switch sends a signal to the electronics when the antenna is in the stowed position 18 or one of the two deployed position 20, 22. Based on this signal, the electronics either prevent RF emission from the antenna when the antenna is in the stowed position 18, or permit RF emission from the antenna when antenna 14 is in either one of the two deployed positions.

Antenna 14 is preferably a coaxial cable whose shield is broken at one point to permit the emission of RF waves. The shield is preferably broken at a location opposite to the pivoting connection 16. The coaxial cable is crimped and soldered to two standard SMB plugs 30, such as those that are commercially available from Huber and Sunher of Switzerland. Thus, the SMB plugs are mechanically and electrically connected to the coaxial cable. A pair of right angle connectors 32 are connected to the printed circuit board 34 within the control unit housing that has the electronics mounted thereon. The right angle connectors 32 are electrically connected to the RF emission/reception electronics, as well as to the SMB plug 30. The SMB plug can freely rotate within the right angle connector without affecting the characteristics of the transmitted wave. A lubricant, such as Spruehoel 88 from Kontact Chemie, Switzerland, can be introduced between the connector and the plug to reduce wear.

Housing 12 has a user interface 26. Electronics 13 are electrically connected to and control user interface 26. The operator may use user interface 26 to input programming operating conditions for the implanted medical device. Interface 26 may include an LCD screen to display information and instructions to the user. A scroll dial and two keys may be used to allow the user to navigate through the menus. Electronics 13 are preferably disposed on a pc board 34 within housing 12. Antenna 14 defines an antenna plane. In the stowed position, the antenna plane is approximately coplanar with a plane defined by the pc board, which is coplanar with the user interface as well. In deployed position 20, the antenna plane is not coplanar with the plane defined by the pc board. But in deployed position 22, the antenna plane is coplanar with the plane defined by the pc board.

Housing 12 is preferably made of a material that shields the electronics from external RF waves, and to decrease emission of un-wanted RF waves from the electronics. In a currently preferred embodiment, the housing is made of plastic. The antenna is preferably a coaxial loop. Antenna 14 is preferably disposed in a housing 28 that permits the transmission and reception of RF waves therethrough.

To use the external control unit to effect communication between an external control unit and an implanted medical device, the user selects the appropriate menu on the user interface of the control unit. The user also places the external control unit within electronic communication range of the implanted medical device. This is preferably achieved by placing the control unit on or near the body closest to where the medical device is implanted within the body. The control unit antenna is moved from the stowed position to a deployed position where RF emission from the antenna is permitted because the electronics detect the position of the antenna. RF waves are emitted from the antenna to establish communication between the external control unit and the implanted medical device. The emitting of RF waves from the antenna is then stopped by the electronics when the communication has successfully been completed. This process usually lasts between 1 and 5 seconds, and the control unit emits an audible beep to indicate to the user that the transmission has ended. Of course, flashing indicating lights, vibrations, or other means may be used to indicate to the user that the transmission has ended. The antenna is then moved to a stowed position where RF emission from the antenna is prevented by the electronics.

Upon detection that the antenna is not in one of the two deployed position, the electronics 13 may cause a menu to be displayed on the interface 26 letting the user know that the antenna must be unfolded before communication can begin. By moving the antenna away from the control unit housing, the tuning of the antenna is improved because the antenna is highly sensitive to metallic objects, such as in the electronics and the display interface.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for effecting communication between an external control unit and an implanted medical device, wherein the external control unit has a housing; electronics disposed on a pc board, for controlling an RF emission from the control unit, are disposed within the housing; an arc shaped antenna is pivotably connected to the housing such that said antenna moves between a stowed position and a deployed position with respect to said housing in only one plane, the arc shaped antenna defines an antenna plane, in the stowed position the antenna plane is approximately coplanar with a plane defined by the pc board, in the stowed position the arc shaped antenna is both approximately coplanar with, and encircles the outer periphery of, the housing, said method comprising the steps of:
   placing the external control unit within electronic communication range of the implanted medical device;
   pivotably moving the control unit arc shaped antenna with respect to said housing in only one plane to a deployed position where RF emission from the arc shaped antenna is permitted; and
   causing the emition of RF waves from the arc shaped antenna to establish communication between the external control unit and the implanted medical device.

2. The method of claim 1, further comprising the steps of:
   causing the stopping of the emition of RF waves from the antenna; and
   pivotably moving the control unit antenna with respect to said housing in only one plane to a stowed position where RF emission from the antenna is prevented.

3. The method of claim 1, further comprising the step of:
   detecting the position of the antenna.

4. The method of claim 3, further comprising the step of:
   preventing the emitting of RF waves from the antenna when the position of the antenna is detected to be in a stowed position.

5. The method of claim 3, further comprising the step of:
   permitting the emitting of RF waves from the antenna when the position of the antenna is detected to be in a deployed position.

6. A method for effecting communication between an external control unit and an implanted medical device, wherein the external control unit has a housing; electronics, for controlling an RF emission from the control unit, are disposed within an enclosed chamber of the housing; an arc shaped antenna is pivotably connected to the housing such that said antenna moves with respect to said housing in only one plane, an arc shaped antenna is pivotably connected to the housing such that said antenna moves between a stowed position and a deployed position, in the stowed position the arc shaped antenna is both approximately coplanar with, and encircles the outer periphery of, the housing, said method comprising the steps of:
   placing the external control unit within electronic communication range of the implanted medical device;
   pivotably moving the control unit arc shaped antenna with respect to said housing in only one plane to a deployed position where RF emission from the antenna is permitted; and
   causing the emition of RF waves from the arc shaped antenna to establish communication between the external control unit and the implanted medical device.

7. The method of claim 6, further comprising the steps of:
   causing the stopping of the emition of RF waves from the antenna; and
   pivotably moving the control unit antenna with respect to said housing in only one plane to a stowed position where RF emission from the antenna is prevented.

8. The method of claim 6, further comprising the step of:
   detecting the position of the antenna.

9. The method of claim 8, further comprising the step of:
   preventing the emitting of RF waves from the antenna when the position of the antenna is detected to be in a stowed position.

10. The method of claim 8, further comprising the step of:
    permitting the emitting of RF waves from the antenna when the position of the antenna is detected to be in a deployed position.

* * * * *